United States Patent
McGowan et al.

(10) Patent No.: US 9,556,199 B2
(45) Date of Patent: Jan. 31, 2017

(54) THIENO[3,2-D]PYRIMIDINES DERIVATIVES FOR THE TREATMENT OF VIRAL INFECTIONS

(71) Applicant: Janssen Sciences Ireland UC, Co Cork (IE)

(72) Inventors: David Craig McGowan, Brussels (BE); Pierre Jean-Marie Bernard Raboisson, Rosieres (BE)

(73) Assignee: JANSSEN SCIENCES IRELAND UC, Little Island, Co Cork (IE)

( * ) Notice: Subject to any disclaimer, the term of this patent is extended or adjusted under 35 U.S.C. 154(b) by 0 days.

(21) Appl. No.: 14/908,237

(22) PCT Filed: Jul. 29, 2014

(86) PCT No.: PCT/EP2014/066219
§ 371 (c)(1),
(2) Date: Jan. 28, 2016

(87) PCT Pub. No.: WO2015/014815
PCT Pub. Date: Feb. 5, 2015

(65) Prior Publication Data
US 2016/0168164 A1   Jun. 16, 2016

(30) Foreign Application Priority Data
Jul. 30, 2013  (EP) .................................. 13178534

(51) Int. Cl.
*A01N 43/90* (2006.01)
*A61K 31/519* (2006.01)
*C07D 491/00* (2006.01)
*C07D 495/00* (2006.01)
*C07D 495/04* (2006.01)

(52) U.S. Cl.
CPC ........... *C07D 495/04* (2013.01); *A61K 31/519* (2013.01)

(58) Field of Classification Search
None
See application file for complete search history.

(56) References Cited

FOREIGN PATENT DOCUMENTS

| EP | 0899263 A3 | 3/1999 |
|----|------------|--------|
| WO | WO98/01448 A1 | 1/1998 |
| WO | WO99/28321 A1 | 6/1999 |
| WO | WO03/055890 A1 | 7/2003 |
| WO | WO2006/117670 A1 | 11/2006 |
| WO | WO2009/067081 A1 | 5/2009 |
| WO | WO2011/062372 A3 | 5/2011 |
| WO | WO2012/136834 A9 | 10/2012 |
| WO | WO2012/156498 A1 | 11/2012 |
| WO | WO2013/068438 A1 | 5/2013 |

OTHER PUBLICATIONS

Chawla et. al. Current Research & Information on Pharmaceutical Science, 2004, 5(1), p. 9, col. 2, para.1.*
Brittain et al., 1999; vol. 95, "Effects of Pharaceutical Processing on drug polymorphs and solvates." in Polymorphism in Pharmaceutical Solids, p. 331-360.*
Newman et. al.; Drug Discovery Today; 2003, 8(19) p. 898, col. 2, Para.3.*
Akira, S., et al., "Toll-Like Receptors", Annu. Rev. Immunology, vol. 21, pp. 335-376 (2003).
Hoffmann, Jules A., "The Immune Response of *Drosophila*", Nature, vol. 426 (2003), pp. 33-38.
Ulevitch, Richard J., "Therapeutics Targeting the Innate Immune System", Nature Reviews, vol. 4, pp. 512-520 (2004).
International Search Report mailed Nov. 13, 2014 for Application No. PCT/EP2014/066219.
Huddleston et al "A Convenient Synthesis of 2-Substituted 3-Hydroxy- and 3-Amino-Thiophens From Derivatives of 2-Chloroacrylic Acid" Synthetic Communications, 1979, vol. 9(8) pp. 731-734.
Barker et al "A Rapid Conversion of 3-Oxothiolanes Into 3-Aminotiophenes" Synthetic Communications 2002 Volme 32(16) pp. 2565-2568.
Abdillahi et al "Synthesis of a Novel Series of Thieno[3,2-D]Pyrimidin-4-(3H)-Ones" Synthesis 2010 vol. 9 pp. 1428-1430 2010.
Extended Search Report for European Application EP 13178534.7 Mailed Jan. 31, 2014.

* cited by examiner

*Primary Examiner* — Jeffrey H Murray

(57) ABSTRACT

This invention relates to thieno[3,2-d]pyrimidines derivatives, processes for their preparation, pharmaceutical compositions, and their use in treating viral infections.

20 Claims, No Drawings

THIENO[3,2-D]PYRIMIDINES DERIVATIVES FOR THE TREATMENT OF VIRAL INFECTIONS

CROSS-REFERENCE TO RELATED APPLICATIONS

This application is the national stage filing under USC 371 of international application PCT/EP2014/066219 filed on Jul. 29, 2014, which claims priority to European Patent Application No. 13178534.7 filed Jul. 30, 2013, the complete disclosures of which are hereby incorporated herein by reference for all purposes.

SEQUENCE LISTING

The instant application contains a Sequence Listing which has been submitted electronically in ASCII format and is hereby incorporated by reference in its entirety. Said ASCII copy, created on Dec. 12, 2016, is named TIP0258USPCT_SL.txt and is 558 bytes in size.

This invention relates to thieno[3,2-d]pyrimidine derivatives, processes for their preparation, pharmaceutical compositions, and their use in treating viral infections.

The present invention relates to the use of thieno[3,2-d] pyrimidine derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behaviour.

It has been estimated that most mammalian species have between ten and fifteen types of Toll-like receptors. Thirteen TLRs (named TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

For reviews on TLRs see the following journal articles. Hoffmann, J. A., Nature, 426, p 33-38, 2003; Akira, S., Takeda, K., and Kaisho, T., Annual Rev. Immunology, 21, p 335-376, 2003; Ulevitch, R. J., Nature Reviews: Immunology, 4, p 512-520, 2004.

Compounds indicating activity on Toll-Like receptors have been previously described such as purine derivatives in WO 2006/117670, adenine derivatives in WO 98/01448 and WO 99/28321, and pyrimidines in WO 2009/067081.

However, there exists a strong need for novel Toll-Like receptor modulators having preferred selectivity, higher potency, and an improved safety profile compared to the compounds of the prior art.

In accordance with the present invention a compound of formula (I) is provided

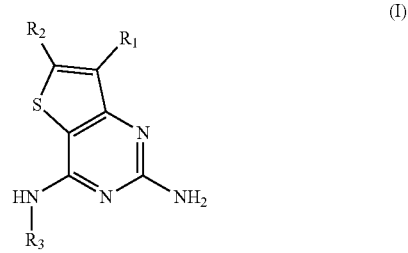

or a pharmaceutically acceptable salt, tautomer(s), stereo-isomeric form, solvate or polymorph thereof, wherein $R_1$ is selected from hydrogen, halogen, —$CH_3$ or —$CF_3$, $R_2$ is selected from hydrogen, halogen, $C_{1-6}$ alkyl or $C_{3-6}$ cycloalkyl, $R_3$ is $C_{1-8}$ alkyl optionally substituted by one or more substituents independently selected from aryl, aryloxy, halogen, hydroxyl, alkylamino, dialkylamino, $C_{1-6}$ alkenyl, $C_{1-6}$ alkoxy, carboxylic acid, carboxylic ester, carboxylic amide, nitrile, sulfonamide, sulfamide, acyl sulfonamide, or $R_3$ is an alkylaryl optionally substituted by one or more substituents independently selected from aryl, aryloxy, halogen, alkylamino, dialkylamino, $C_{1-6}$ alkyl, $C_{1-6}$ alkenyl, $C_{1-6}$ alkoxy, carboxylic acid, carboxylic ester, carboxylic amide, nitrile, sulfonamide, sulfamide, or acyl sulfonamide.

The compounds of formula (I) and their pharmaceutically acceptable salts, tautomer(s), stereo-isomeric forms, solvate or polymorph thereof have activity as pharmaceuticals, in particular as modulators of Toll-Like Receptors 7 and 8 (especially TLR 8).

In a further aspect the present invention provides a pharmaceutical composition comprising a compound of formula (I) or a pharmaceutically acceptable salt, tautomer, stereo-isomeric form, solvate or polymorph thereof together with one or more pharmaceutically acceptable excipients, diluents or carriers.

Furthermore a compound of formula (I) or a pharmaceutically acceptable salt, solvate, tautomer, stereo-isomeric form or polymorph thereof according to the current invention, or a pharmaceutical composition comprising said compound of formula (I) or a pharmaceutically acceptable salt, solvate, tautomer, stereo-isomeric form or polymorph thereof can be used as a medicament.

Another aspect of the invention is that a compound of formula (I) or its pharmaceutically acceptable salt, solvate, tautomer, stereo-isomeric form or polymorph thereof, or said pharmaceutical composition comprising said compound of formula (I) or a pharmaceutically acceptable salt, solvate, tautomer, stereo-isomeric form or polymorph thereof can be used accordingly in the treatment of a disorder in which the modulation of TLR7 and/or TLR8 is involved preferably TLR8.

The term "($C_{1-8}$)-alkyl" and "($C_{1-6}$)-alkyl" refers to a straight-chain, branched-chain or cyclic saturated aliphatic hydrocarbon containing the specified number of carbon atoms.

The term "halogen" refers to fluorine, chlorine, bromine or iodine.

The term "alkylaryl" refers to a straight-chain or branched-chain saturated aliphatic hydrocarbon containing the specified number of carbon atoms substituted by an aryl wherein "aryl" is defined as below.

The term "alkenyl" refers to an alkyl as defined above consisting of at least two carbon atoms and at least one carbon-carbon double bond.

The term "cycloalkyl" refers to a carbocyclic ring containing the specified number of carbon atoms.

The term "alkoxy" refers to an alkyl (carbon and hydrogen chain) group singular bonded to oxygen like for instance a methoxy group or ethoxy group.

The term "aryl" means an aromatic ring structure optionally comprising one or two heteroatoms selected from N, O and S, in particular from N and O. Said aromatic ring structure may have 5, 6 or 7 ring atoms. In particular, said aromatic ring structure may have 5 or 6 ring atoms.

The term "aryloxy" refers to an aromatic ring structure. Said aromatic group is singularly bonded to oxygen.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other.

A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration. If a compound contains an at least disubstituted non-aromatic cyclic group, the substituents may be in the cis or trans configuration.

Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

Preparation of Compounds of Formula (I)
Overall Scheme.

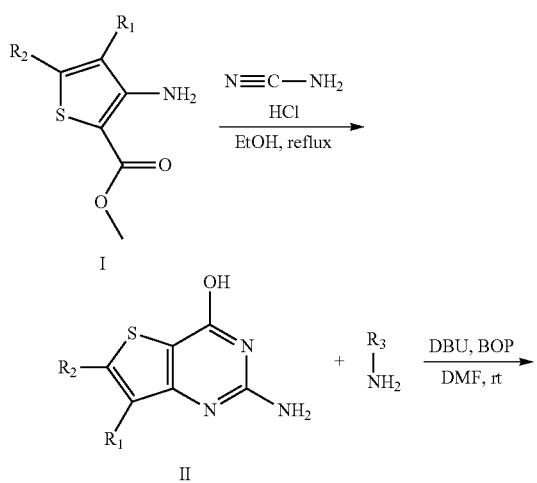

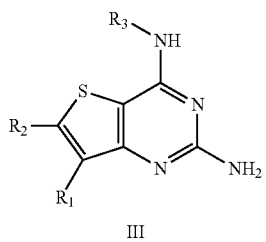

The preparation of compounds of type I are described in the literature (Synthetic Communications, 9(8), p 731-4, 1979; Synthetic Communications, 32(16), 2565-2568; 2002). 3-aminothiophene-2-carboxylates are mixed with cyanamide in a polar solvent (e.g. ethanol) containing acid (e.g. HCl) to form intermediates II with heat as described in the literature (Synthesis, (9), p 1428, 2010). Intermediate II in polar, aprotic solvent can be mixed with BOP or PyBOP in combination with a base (e.g. DBU) and the amine to lead to the formation of final products (III) at room temperature. Alternatively, the alcohol in intermediates of type II can be converted to chlorine using described methods and chlorinating agents, such as POCl$_3$, often with heat and in the presence of solvent, and optionally with base. After isolation, the 4-chloro intermediate can then be used to form products of type III by heating with the amine in base and polar solvent (e.g. acetonitrile).

Preparation of 1

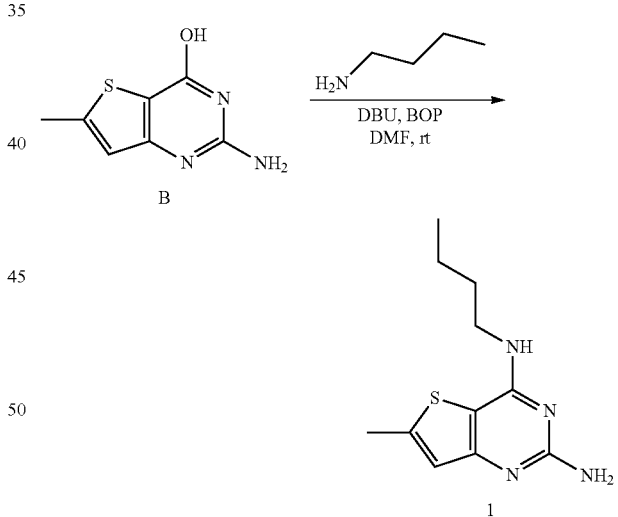

Into a 50 mL glass vial was placed B (500 mg, 2.76 mmol), anhydrous DMF (5 mL), DBU (1.26 g, 8.28 mmol), n-butylamine (605 mg, 8.3 mmol), and BOP (1.46 g, 3.31 mmol). The vial was sealed and shaken for 16 hours at room temperature. LC-MS showed conversion to product. The crude reaction mixture was purified by preparatory HPLC (RP SunFire Prep C18 OBD-10 μm, 30×150 mm, mobile phase 0.25% aq. ammonium carbonate, to acetonitrile). The best fractions were pooled and the solvents were removed under reduced pressure to afford a white solid, 1. LC-MS m/z=237 (M+H).

TABLE 1

Compounds of formula (I) and corresponding analytical data. Compounds were prepared according to the methods described in the experimental section.

| # | STRUCTURE | $^1$H NMR | LC Method, Rt (min) | LC-MS Mass Found (M + H) |
|---|---|---|---|---|
| 1 | 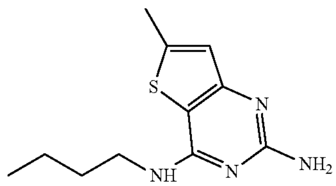 [SMILES: CCCCNc1nc(N)nc2cc(C)sc12] | $^1$H NMR (400 MHz, DMSO-d$_6$) δ ppm 0.91 (t, J = 7.4 Hz, 3 H), 1.33 (dq, J = 14.9, 7.4 Hz, 2 H), 1.49-1.61 (m, 2 H), 3.35 (s, 3 H), 3.36-3.42 (m, 2 H), 5.74 (s, 2 H), 6.69 (s, 1 H), 7.03 (t, J = 5.5 Hz, 1 H) | A, 0.8 | 237 |
| 2 | 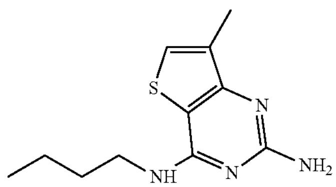 [SMILES: CCCCNc1nc(N)nc2c(C)csc12] | $^1$H NMR (400 MHz, DMSO-d$_6$) δ ppm 0.91 (t, J = 7.4 Hz, 3 H), 1.26-1.42 (m, 2 H), 1.48-1.62 (m, 2 H), 2.17 (d, J = 1.1 Hz, 3 H), 3.37-3.46 (m, 2 H), 5.83 (s, 2 H), 7.14 (s, 1 H), 7.43 (d, J = 1.1 Hz, 1 H) | B, 1.52 | 237 |
| 3 | 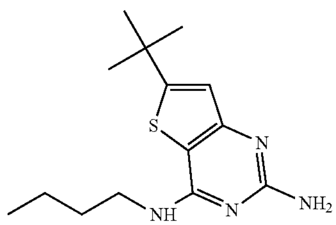 [SMILES: CCCCNc1nc(N)nc2cc(C(C)(C)C)sc12] | $^1$H NMR (400 MHz, DMSO-d$_6$) δ ppm 0.90 (t, J = 7.4 Hz, 3 H), 1.27-1.35 (m, 2 H), 1.36 (s, 9 H), 1.47-1.60 (m, 2 H), 3.35-3.43 (m, 2 H), 5.72 (s, 2 H), 6.73 (s, 1 H), 7.04 (t, J = 5.5 Hz, 1 H) | B, 1.83 | 279 |
| 4 | 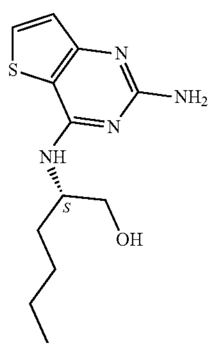 | $^1$H NMR (400 MHz, DMSO-d$_6$) δ ppm 0.85 (br. s., 3H), 1.17-1.39 (m, 4 H), 1.43-1.56 (m, 1 H), 1.65 (br. s., 1 H), 3.39-3.54 (m, 2 H), 4.26 (d, J = 4.4 Hz, 1 H), 4.65 (br. s., 1 H), 5.75 (s, 2 H), 6.84 (d, J = 8.4 Hz, 1 H), 6.95 (d, J = 5.3 Hz, 1 H), 7.81 (d, J = 5.3 Hz, 1 H) | A, 0.70 | 267 |
| 5 | 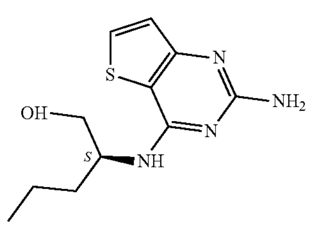 | $^1$H NMR (400 MHz, DMSO-d$_6$) δ ppm 0.78-0.94 (m, 3 H), 1.16-1.41 (m, 2 H), 1.45-1.69 (m, 2 H), 3.47-3.53 (m, 1 H), 4.30-4.47 (m, 2 H), 7.18-7.28 (m, 1 H), 7.77 (br. s., 2 H), 8.18 (d, J = 5.3 Hz, 1 H), 8.92 (d, J = 8.4 Hz, 1 H), 13.26 (br. s., 1 H) | A, 0.63 | 253 |
| 6 | 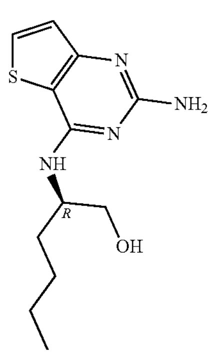 | $^1$H NMR (400 MHz, DMSO-d$_6$) δ ppm 0.84 (br. s., 3 H), 1.19-1.39 (m, 4 H), 1.42-1.57 (m, 1 H), 1.65 (br. s., 1 H), 3.37-3.55 (m, 2 H), 3.71-4.21 (m, 1 H), 4.28 (d, J = 4.6 Hz, 1 H), 5.97 (br. s., 2 H), 6.97 (d, J = 5.3 Hz, 1 H), 7.05 (d, J = 8.4 Hz, 1 H), 7.84 (d, J = 5.3 Hz, 1 H) | A, 0.70 | 267 |

TABLE 1-continued

Compounds of formula (I) and corresponding analytical data. Compounds were prepared according to the methods described in the experimental section.

| # | STRUCTURE | ¹H NMR | LC Method, Rt (min) | LC-MS Mass Found (M + H) |
|---|---|---|---|---|
| 7 | 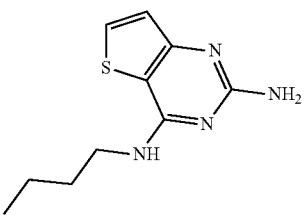 | ¹H NMR (400 MHz, CHLOROFORM-d) δ ppm 0.98 (t, J = 7.4 Hz, 3 H), 1.39-1.51 (m, 2 H). 1.61-1.69 (m, 2 H), 1.74 (s, 1 H), 3.59 (td, J = 7.2, 5.7 Hz, 2 H), 4.71 (br. s.,2 H), 7.11 (d, J = 5.3 Hz, 1 H), 7.56 (d, J = 5.3 Hz, 1 H) | B, 0.71 | 223 |
| 8 | 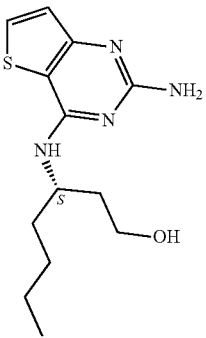 | ¹H NMR (400 MHz, DMSO-$d_6$) δ ppm 0.81-0.93 (m, 3 H), 1.20-1.40 (m, 4 H), 1.52-1.65 (m, 2 H), 1.74 (q, J = 6.6 Hz, 2 H), 3.40-3.50 (m, 2 H), 4.38-4.52 (m, 2 H), 7.22 (d, J = 5.5 Hz, 1 H),7.63-7.82 (m, 2 H), 8.18 (d, J = 5.5 Hz, 1 H), 8.82 (d, J = 8.4 Hz, 1 H) | A, 0.76 | 281 |
| 9 | 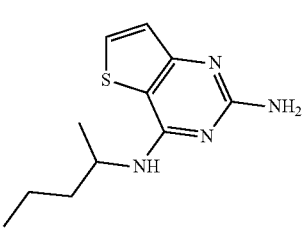 [SMILES: CCCC(C)Nc1nc(N)nc2ccsc12] | ¹H NMR (400 MHz, DMSO-$d_6$) δ ppm 0.89 (t, J = 7.3 Hz, 3 H), 1.16 (d, J = 6.6 Hz, 3 H), 1.26-1.38 (m, 2 H), 1.39-1.51 (m, 1 H), 1.53-1.64 (m, 1 H), 4.28-4.39 (m, 1 H), 5.77 (s, 2 H), 6.95 (d, J = 5.3 Hz, 1 H), 7.01 (d, J = 8.4 Hz, 1 H), 7.81 (d, J = 5.3 Hz, 1 H) | A, 0.82 | 237 |
| 10 | 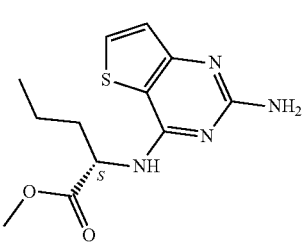 | ¹H NMR (400 MHz, DMSO-$d_6$) δ ppm 0.84-0.98 (m, 3 H), 1.27-1.51 (m, 2 H), 1.57-1.70 (m, 1 H), 1.80-1.98 (m, 1 H), 3.69 (s, 3 H), 4.76-4.92 (m, 1 H), 7.27 (d, J = 5.3 Hz, 1 H), 7.89 (br. s., 2 H), 8.26 (d, J = 5.3 Hz, 1 H), 9.47 (d, J = 7.3 Hz, 1 H) | A, 0.76 | 281 |
| 11 | 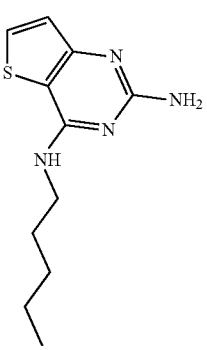 [SMILES: CCCCCNc1nc(N)nc2ccsc12] | ¹H NMR (400 MHz, DMSO-$d_6$) δ ppm 0.87 (t, J = 6.9 Hz, 3 H), 1.25-1.37 (m, 4 H), 1.57 (br. s., 2 H), 3.39-3.44 (m, 2 H), 5.80 (s, 2 H), 6.95 (d, J = 5.3 Hz, 1 H), 7.25 (s, 1 H), 7.80 (d, J = 5.3 Hz, 1 H) | A, 0.84 | 237 |

TABLE 1-continued

Compounds of formula (I) and corresponding analytical data. Compounds were prepared according to the methods described in the experimental section.

| # | STRUCTURE | ¹H NMR | LC Method, Rt (min) | LC-MS Mass Found (M + H) |
|---|---|---|---|---|
| 12 | 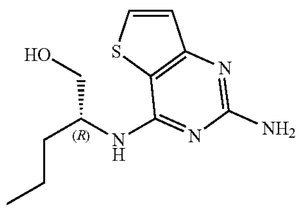 | ¹H NMR (400 MHz, DMSO-d$_6$) δ ppm 0.88 (t, J = 7.3 Hz, 3 H), 1.21-1.43 (m, 2 H), 1.50 (dtd, J = 13.5, 9.0, 9.0, 5.0 Hz, 1 H), 1.57-1.69 (m, 1 H), 3.38-3.53 (m, 2 H), 4.29 (d, J = 4.6 Hz, 1 H), 4.62 (br. s., 1 H), 5.80 (s, 2 H), 6.87 (d, J = 8.4 Hz, 1 H), 6.96 (d, J = 5.3 Hz, 1 H), 7.82 (d, J = 5.3 Hz, 1 H) | A, 0.61 | 253.1 |
| 13 | 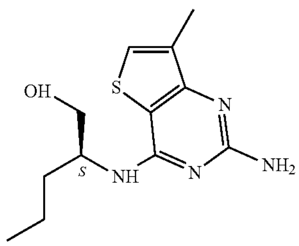 | ¹H NMR (400 MHz, CHLOROFORM-d) δ ppm 0.95 (t, J = 7.3 Hz, 3 H), 1.32-1.50 (m, 2 H), 1.51-1.71 (m, 2 H), 2.31 (d, J = 1.1 Hz, 3 H), 3.34 (s, 1 H), 3.67 (dd, J = 11.0, 6.4 Hz, 1 H), 3.83 (dd, J = 11.0, 3.3 Hz, 1 H), 4.19-4.38 (m, 1 H), 4.77 (d, J = 7.3 Hz, 1 H), 4.87 (s, 2 H), 7.19 (d, J = 1.1 Hz, 1 H) | A, 0.67 | 267.1 |
| 14 | 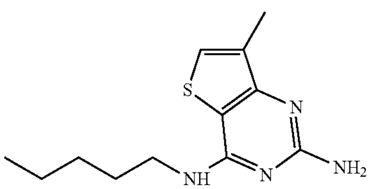 [SMILES: CCCCCNc1nc(N)nc2c(C)csc12] | ¹H NMR (400 MHz, DMSO-d$_6$) δ ppm 0.80-0.94 (m, 3 H), 1.20-1.39 (m, 4 H), 1.49-1.64 (m, 2 H), 2.17 (d, J = 1.1 Hz, 3 H), 3.36-3.43 (m, 2 H), 5.82 (s, 2 H), 7.15 (t, J = 5.5 Hz, 1 H), 7.43 (d, J = 1.1 Hz, 1 H) | B, 1.69 | 251.0 |
| 15 | 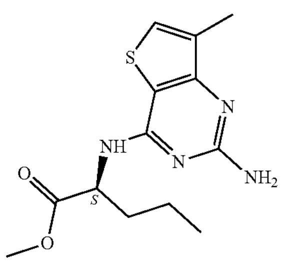 | ¹H NMR (400 MHz, CHLOROFORM-d) δ ppm 0.96 (t, J = 7.4 Hz, 3 H), 1.22-1.33 (m, 1 H), 1.35-1.52 (m, 1 H), 1.74-1.86 (m, 1 H), 1.87-2.01 (m, 1 H), 2.33 (d, J = 1.1 Hz, 3 H), 3.76 (s, 3 H), 4.75 (br. s., 2 H), 4.97 (td, J = 7.5, 5.6 Hz, 1 H), 5.10 (d, J = 7.7 Hz, 1 H), 7.22 (d, J = 1.1 Hz, 1 H) | E, 1.02 | 295.2 |
| 16 | 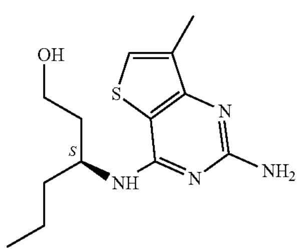 | ¹H NMR (400 MHz, CHLOROFORM-d) δ ppm 0.92 (t, J = 7.4 Hz, 3 H), 1.26-1.50 (m, 3 H), 1.51-1.66 (m, 2 H), 1.68-1.79 (m, 1 H), 1.86-2.03 (m, 1 H), 2.32 (d, J = 1.1 Hz, 3 H), 3.45-3.68 (m, 2 H), 4.41 (ddd, J = 11.1, 5.4, 2.9 Hz, 1 H), 4.52 (d, J = 8.8 Hz, 1 H), 4.97 (s, 2 H), 7.20 (d, J = 1.1 Hz, 1 H) | A, 0.72 | 281.2 |
| 17 | 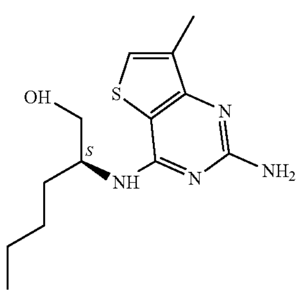 | | B, 1.38 | 281.1 |

TABLE 1-continued

Compounds of formula (I) and corresponding analytical data. Compounds were prepared according to the methods described in the experimental section.

| # | STRUCTURE | ¹H NMR | LC Method, Rt (min) | LC-MS Mass Found (M + H) |
|---|---|---|---|---|
| 18 | 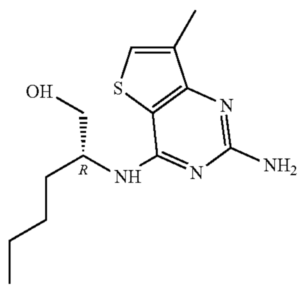 | 1H NMR (400 MHz, DMSO-d6) δ ppm 0.85 (t, J = 6.5 Hz, 3 H), 1.11-1.35 (m, 4 H), 1.38-1.56 (m, 1 H), 1.57-1.74 (m, 1 H), 2.18 (d, J = 0.9 Hz, 3 H), 3.39-3.55 (m, 2 H), 4.19-4.35 (m, 1 H), 4.66 (br. s., 1 H), 5.79 (s, 2 H), 6.75 (d, J = 8.4 Hz, 1 H), 7.44 (d, J = 1.1 Hz, 1 H) | B, 1.41 | 281.1 |
| 19 | 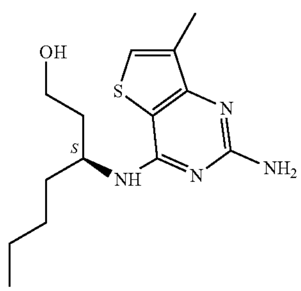 | ¹H NMR (400 MHz, DMSO-$d_6$) δ ppm 0.76-0.91 (m, 3 H), 1.16-1.36 (m, 4 H), 1.44-1.58 (m, 2 H), 1.59-1.79 (m, 2 H), 2.17 (d, J = 1.1 Hz, 3 H), 3.38-3.49 (m, 2 H), 4.34 (d, J = 7.5 Hz, 1 H), 4.40 (t, J = 5.4 Hz, 1 H), 5.83 (s, 2 H), 6.87 (d, J = 8.6 Hz, 1 H), 7.44 (d, J = 1.1 Hz, 1 H) | B, 1.49 | 295.1 |
| 20 | 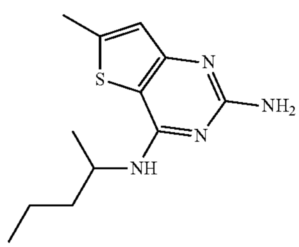 [SMILES: CCCC(C)Nc1nc(N)nc2cc(C)sc12] | ¹H NMR (400 MHz, DMSO-$d_6$) δ ppm 0.88 (t, J = 7.3 Hz, 3 H), 1.18 (d, J = 6.5 Hz, 3 H), 1.23-1.38 (m 2 H), 1.40-1.69 (m, 2 H), 2.58 (s, 3 H), 4.25-4.45 (m, 1 H), 6.93 (s, 1 H), 7.50 (br. s., 2 H), 8.50 (br. s., 1 H) | B, 1.66 | 251.1 |
| 21 | 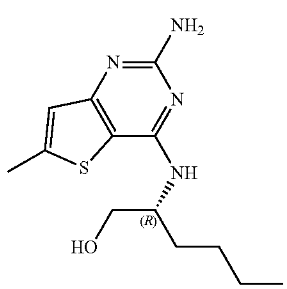 | ¹H NMR (400 MHz, DMSO-$d_6$) ☐ ppm 0.85 (t, J = 6.5 Hz, 3 H), 1.17-1.40 (m, 4 H), 1.43-1.71 (m, 2 H), 2.59 (s, 3 H), 3.45-3.50 (m, 2 H), 4.20-4.41 (m, 1 H), 6.99 (d, J = 0.8 Hz, 1 H), 7.66 (br. s., 2 H), 8.71 (d, J = 8.5 Hz, 1 H), 13.00 (br. s., 1 H) | D, 2.49 | 281.1 |
| 22 | 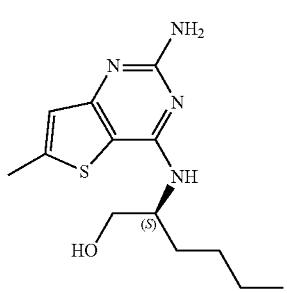 | ¹H NMR (400 MHz, DMSO-$d_6$) δ ppm 0.85 (t, J = 6.7 Hz, 3 H), 1.08-1.38 (m, 4 H), 1.43-1.71 (m, 2 H), 2.52 (br. s., 2 H), 2.57 (m, J = 1.0 Hz, 3 H), 4.29 (d, J = 5.0 Hz, 1 H), 4.82 (br. s., 1 H), 6.92 (d, J = 1.3 Hz, 1 H), 7.20 (br. s., 2 H), 8.22 (br. s., 1 H) | D, 2.67 | 281.1 |

TABLE 1-continued

Compounds of formula (I) and corresponding analytical data. Compounds were prepared according to the methods described in the experimental section.

| # | STRUCTURE | $^1$H NMR | LC Method, Rt (min) | LC-MS Mass Found (M + H) |
|---|---|---|---|---|
| 23 | (structure) | $^1$H NMR (400 MHz, DMSO-d$_6$) δ ppm 0.85 (t, J = 6.8 Hz, 3 H), 1.16-1.35 (m, 4 H), 1.40 (s, 9 H), 1.51 (dd, J = 9.0, 4.8 Hz, 1 H), 1.64 (d, J = 6.0 Hz, 1 H), 3.47 (br. s., 2 H), 4.33 (d, J = 4.8 Hz, 1 H), 4.83 (br. s., 1 H), 7.00 (s, 1 H), 7.67 (br. s., 2 H), 8.66 (d, J = 8.5 Hz, 1 H) | C, 2.67 | 323.1 |

Analytical Methods

General information: the LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas.

LC-MS Methods.

| LC-MS Method code | Column | Mobile phase | Gradient | Flow (mL/min)/ Temp (° C.) | Run time (min) |
|---|---|---|---|---|---|
| A | Waters: BEH C18 (1.7 μm, 2.1 × 50 mm) | A: 10 mM CH$_3$COONH$_4$ in 95% H$_2$O + 5% CH$_3$CNB: CH$_3$CN | From 95% A to 5% A in 1.3 min, held for 0.7 min. | 0.8/55 | 2 |
| B | Waters: HSS T3 (1.8 μm, 2.1 × 100 mm) | A: 10 mM CH$_3$COONH$_4$ in 95% H$_2$O + 5% CH$_3$CN B: CH$_3$CN | From 100% A to 5% A in 2.10 min, to 0% A in 0.90 min, to 5% A in 0.5 min | 0.8/55 | 3.5 |
| C | Agilent: TC-C18 (5 μm, 2.1 × 50 mm) | A: CF$_3$COOH 0.1% in water, B: CF$_3$COOH 0.05% in CH$_3$CN | 100% A for 1 min, to 40% A in 4 min, to15% A in 2.5 min, to 100% A in 2 min | 0.8/50 | 10.5 |
| D | Agilent: TC-C18 (5 μm, 2.1 × 50 mm) | A: CF$_3$COOH 0.1% in water, B: CF$_3$COOH 0.05% in CH$_3$CN | 90% A for 0.8 min, to 20% A in 3.7 min, held for 3 min, back to 90% A in 2 min. | 0.8/50 | 10.5 |
| E | Waters: BEH C18 (1.7 μm, 2.1*50 mm) | A: 10 mM CH$_3$COONH$_4$ in 90% H$_2$O + 10% CH$_3$CN B: MeOH | From 95% A to 5% A in 1.3 min, held for 0.2 min to 95% A in 0.2 min held for 0.1 min. | 0.7/70 | 1.8 |

Biological Activity of Compounds of Formula (I)

Description of Biological Assays

Assessment of TLR7 and TLR8 Activity

The ability of compounds to activate human TLR7 and/or TLR8 was assessed in a cellular reporter assay using HEK293 cells transiently transfected with a TLR7 or TLR8 expression vector and NFκB-luc reporter construct.

Briefly, HEK293 cells were grown in culture medium (DMEM supplemented with 10% FCS and 2 mM Glutamine). For transfection of cells in 15 cm dishes, cells were detached with Trypsin-EDTA, transfected with a mix of CMV-TLR7 or TLR8 plasmid (1700 ng), NFκB-luc plasmid (850 ng) and a transfection reagent and incubated for 48 h at 37° C. in a humidified 5% CO$_2$ atmosphere. Transfected cells were then washed in PBS, detached with Trypsin-EDTA and resuspended in medium to a density of $1.25 \times 10^5$ cells/mL. Forty microliters of cells were then dispensed into each well in 384-well plates, where 200 nL of compound in 100% DMSO was already present. Following 6 hours incubation at 37° C., 5% CO$_2$, the luciferase activity was determined by adding 15 μL of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound.

Compound toxicity was determined in parallel using a similar dilution series of compound with 40 μL per well of cells transfected with the CMV-TLR7 construct alone ($1.25 \times 10^5$ cells/mL), in 384-well plates. Cell viability was measured after 6 hours incubation at 37° C., 5% CO$_2$ by adding 15 μL of ATP lite (Perkin Elmer) per well and reading on a ViewLux ultraHTS microplate imager (Perkin Elmer). Data was reported as CC$_{50}$.

In parallel, a similar dilution series of compound was used (200 nL of compound in 100% DMSO) with 40 μL per well of cells transfected with NFκB-luc reporter construct alone ($1.25 \times 10^5$ cells/mL). Six hours after incubation at 37° C., 5% CO$_2$, the luciferase activity was determined by adding 15 μl of Steady Lite Plus substrate (Perkin Elmer) to each well and readout performed on a ViewLux ultraHTS microplate imager (Perkin Elmer). Counterscreen data is reported as LEC.

Activation of ISRE Promoter Elements

The potential of compounds to induce IFN-I was also evaluated by measuring the activation of interferon-stimulated responsive elements (ISRE) by conditioned media from PBMC. The ISRE element of sequence GAAACT-GAAACT (SEQ ID NO: 1) is highly responsive to the STAT1-STAT2-IRF9 transcription factor, activated upon binding of IFN-I to their receptor IFNAR (Clontech, PT3372-5W). The plasmid pISRE-Luc from Clontech (ref. 631913) contains 5 copies of this ISRE element, followed by the firefly luciferase ORF. A HEK293 cell line stably transfected with pISRE-Luc (HEK-ISREluc) was established to profile the conditioned PBMC cell culture media.

Briefly, PBMCs were prepared from buffy coats of at least two donors using a standard Ficoll centrifugation protocol. Isolated PBMCs were resuspended in RPMI medium supplemented with 10% human AB serum and $2 \times 10^5$ cells/well were dispensed into 384-well plates containing compounds (70 μL total volume). After overnight incubation, 10 μL of supernatant was transferred to 384-well plates containing $5 \times 10^3$ HEK-ISREluc cells/well in 30 μL (plated the day before). Following 24 hours of incubation, activation of the ISRE elements was measured by assaying luciferase activity using 40 μL/well Steady Lite Plus substrate (Perkin Elmer) and measured with ViewLux ultraHTS microplate imager (Perkin Elmer). The stimulating activity of each compound on the HEK-ISREluc cells was reported as LEC value, defined as the compound concentration applied to the PBMCs resulting in a luciferase activity at least two fold above the standard deviation of the assay. The LEC in turn indicates the degree of ISRE activation on transfer of a defined amount of PBMC culture medium. Recombinant interferon α-2a (Roferon-A) was used as a standard control compound.

TABLE 2

Biological Activity of compounds of formula (I).

| # | Human TLR 7 (LEC) μM | Human TLR 8 (LEC) μM | HEK-ISRE luc (LEC) μM |
|---|---|---|---|
| 1 | 1.0 | 0.5 | 0.1 |
| 2 | 2.2 | 1.0 | 0.6 |
| 3 | 1.2 | 1.2 | 0.4 |
| 4 | 0.5 | 0.03 | 0.04 |
| 5 | 2.7 | 0.2 | 0.4 |
| 6 | >25 | 0.5 | 0.6 |
| 7 | 1.1 | 0.7 | 0.3 |
| 8 | 1.2 | 0.7 | 0.3 |
| 9 | 3.3 | 2.5 | 3.8 |
| 10 | 6.1 | 2.7 | 0.8 |
| 11 | 2.1 | 3.9 | 1.2 |
| 12 | >25 | 7.2 | 21 |
| 13 | 12 | 0.2 | 0.6 |
| 14 | 6.8 | 1.9 | 3.2 |
| 15 | >25 | 3.5 | 2.6 |
| 16 | 5.2 | 1.6 | 0.7 |
| 17 | 3.7 | 0.3 | 0.4 |
| 18 | >25 | 0.8 | 1.7 |
| 19 | 3.9 | 1.6 | 0.6 |
| 20 | >25 | 6.9 | 10.1 |
| 21 | 10.4 | 0.6 | — |
| 22 | 2.9 | 0.2 | — |
| 23 | 2.7 | 2.6 | — |

All compounds showed no activity (LEC >25 μM) in the HEK 293 NF-kB counterscreen assay described above.

The invention claimed is:

1. A compound of formula (I)

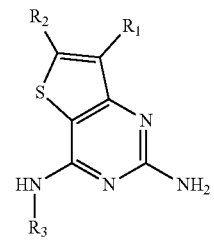

or a pharmaceutically acceptable salt, tautomer(s), stereoisomeric form, or solvate thereof, wherein $R_1$ is selected from the group consisting of hydrogen, halogen, —$CH_3$ and —$CF_3$;

$R_2$ is selected from the group consisting of hydrogen, halogen, $C_{1-6}$ alkyl and $C_{3-6}$ cycloalkyl;

$R_3$ is $C_{1-8}$ alkyl optionally substituted by one or more substituents independently selected from the group consisting of aryl, aryloxy, halogen, hydroxyl, alkylamino, dialkylamino, $C_{1-6}$ alkenyl, $C_{1-6}$ alkoxy, —$CO_2H$, —$CO_2C_{1-6}$ alkyl, —$CO_2NH_2$, —CN, —$SO_2NHC_{1-3}$alkyl, —$NHSO_2C_{1-3}$alkyl, —$NH(SO_2)NH_2$, and —$SO_2N(H)(COC_{1-6}$ alkyl; or $R_3$ is an alkylaryl optionally substituted by one or more substituents independently selected from the group consisting of aryl, aryloxy, halogen, alkylamino, dialkylamino, $C_{1-6}$ alkyl, $C_{1-6}$ alkenyl, $C_{1-6}$ alkoxy, —$CO_2H$, —$CO_2C_{1-6}$ alkyl, —$CO_2NH_2$, —CN, —$SO_2NHC_{1-3}$alkyl, —$NHSO_2C_{1-3}$alkyl, —$NH(SO_2)NH_2$, and —$C(O)NHSO_2C_{1-3}$alkyl.

2. A compound according to claim 1 wherein $R_1$ and $R_2$ are both hydrogen and wherein $R_3$ is $C_{1-8}$ alkyl substituted by hydroxyl.

3. A compound according to claim 2 having the structure

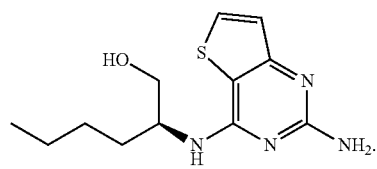 [SMILES: CCCC[C@@H](CO)Nc1nc(N)nc2ccsc12]

4. A pharmaceutical composition comprising a compound according to claim 1 together with one or more pharmaceutically acceptable excipients, diluents or carriers.

5. A method of treating a disorder in which the modulation of TLR 7 and/or TLR 8 is involved, comprising the administration of a therapeutically effective amount of at least one compound of claim 1.

6. The method of claim 5, wherein the disorder is a viral infection.

7. A compound according to claim 1 having the structure

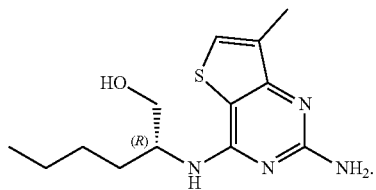

8. A compound according to claim 1, wherein $R_2$ is H, $CH_3$ or $C(CH_3)_3$.

9. A compound according to claim 1, wherein $R_3$ is selected from the group consisting of

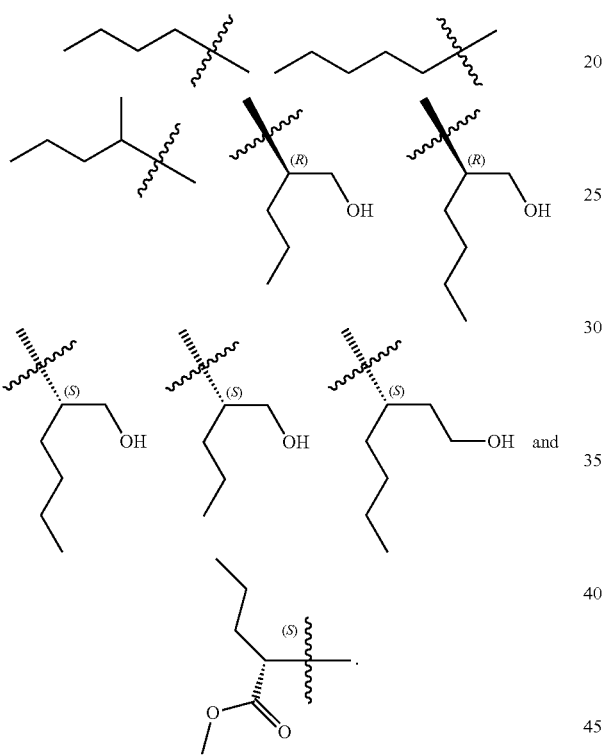

10. A compound according to claim 1 wherein $R_1$ is H and $R_2$ is $CH_3$.

11. A compound according to claim 1 wherein $R_1$ is $CH_3$ and $R_2$ is H.

12. A compound according to claim 1 wherein $R_1$ and $R_2$ are H.

13. A compound according to claim 1, wherein $R_3$ is selected from the group consisting of

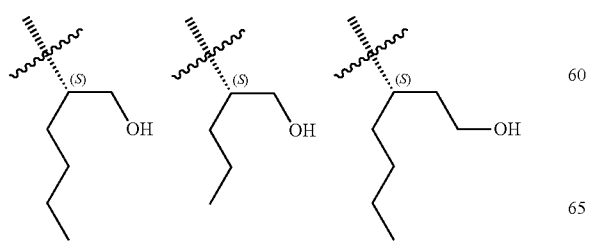

-continued

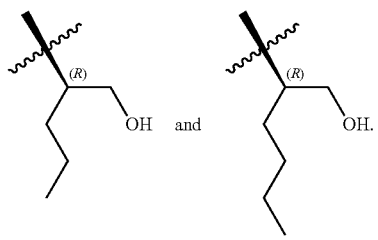

14. A compound according to claim 1, wherein $R_3$ is

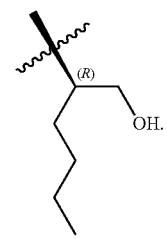

15. A compound according to claim 1, wherein said compound is selected from the group consisting of

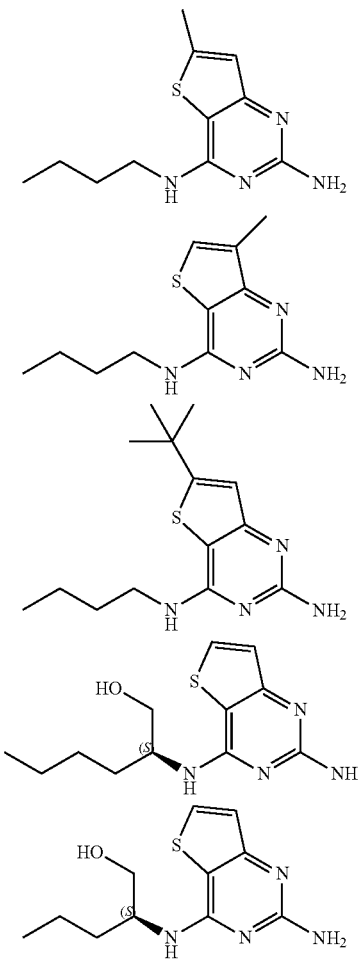

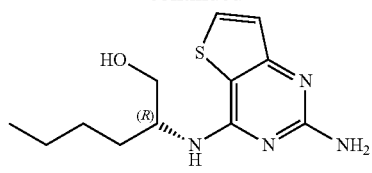
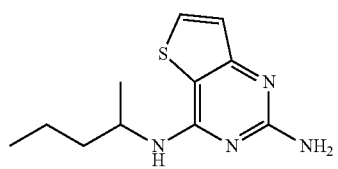
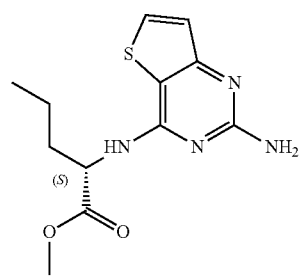
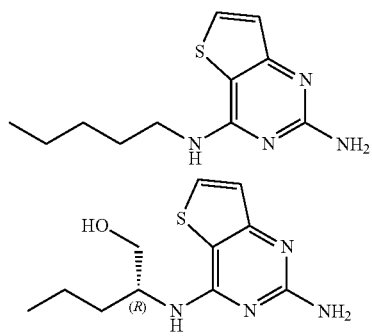
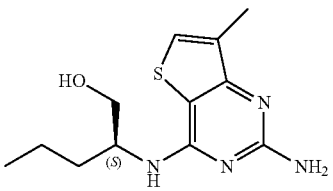
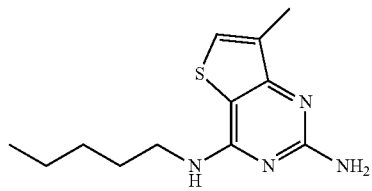
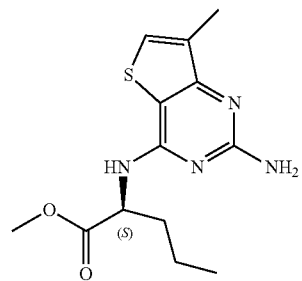
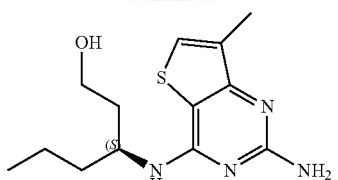
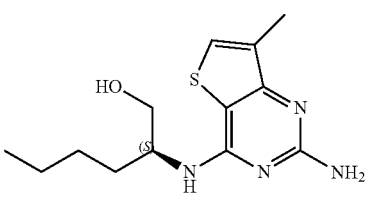
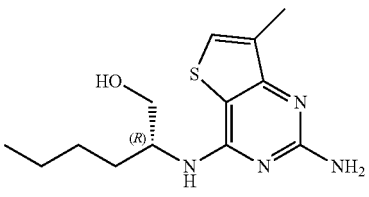
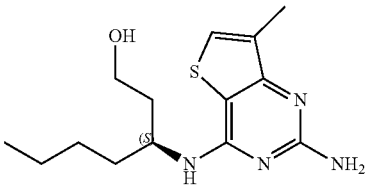
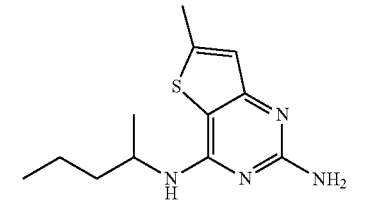
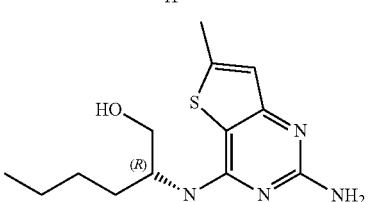
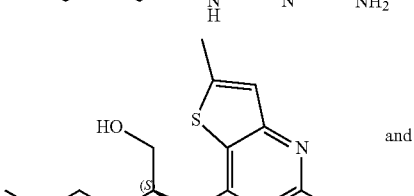
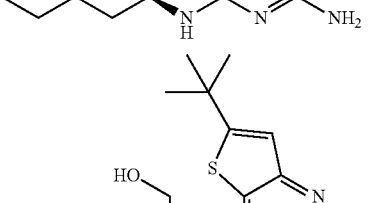
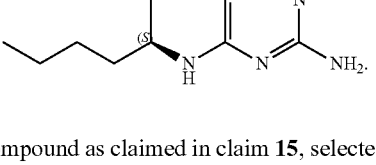
16. A compound as claimed in claim 15, selected from the group consisting of

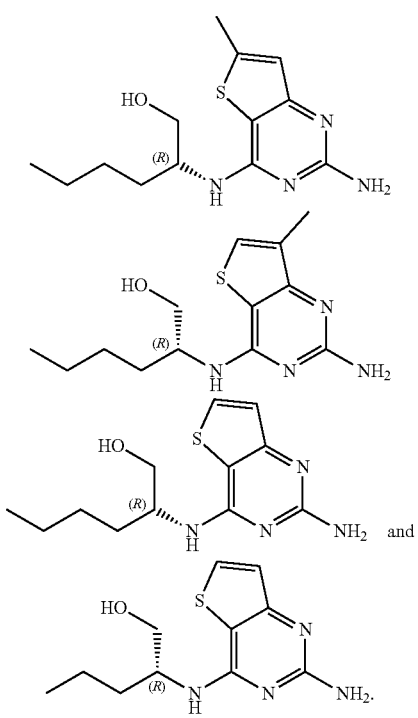

17. A pharmaceutical composition comprising a compound according to claim 15 together with one or more pharmaceutically acceptable excipients, diluents or carriers.

18. A method of treating a disorder in which the modulation of TLR 7 and/or TLR 8 is involved, comprising the administration of a therapeutically effective amount of at least one compound as claimed in claim 15.

19. The method of claim 18, wherein the disorder is a viral infection.

20. A method of preparing a compound of claim 1, wherein said method comprises:

mixing intermediate I with cyanamide in a polar solvent containing acid to form intermediate II

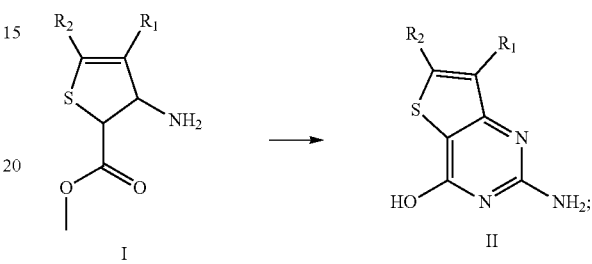

and mixing intermediate II with a peptide coupling reagent or a chlorinating agent in combination with a base and an amine in a polar solvent to form the compound of claim 1.

* * * * *